United States Patent [19]

Kearns

[11] Patent Number: 4,494,059
[45] Date of Patent: Jan. 15, 1985

[54] STRUCTURE FOR AND METHOD OF SURFACE CONDITIONING SENSING AND INDICATING AND MOTOR SPEED CONTROL

[76] Inventor: Robert W. Kearns, 9725 Lookout Pl., Gaithersburg, Md. 20760

[21] Appl. No.: 110,714

[22] Filed: Jan. 9, 1980

Related U.S. Application Data

[60] Continuation of Ser. No. 957,775, Nov. 6, 1978, which is a continuation of Ser. No. 814,000, Jul. 8, 1977, which is a continuation of Ser. No. 565,478, Apr. 7, 1975, , which is a continuation of Ser. No. 340,557, Mar. 12, 1973, Pat. No. 3,876,919, which is a division of Ser. No. 487,795, Jun. 8, 1970, Pat. No. 3,721,115, which is a continuation of Ser. No. 666,703, Sep. 11, 1967, abandoned.

[51] Int. Cl.³ .............................................. H02P 1/04
[52] U.S. Cl. .................................. 318/443; 318/331; 318/491; 318/361
[58] Field of Search ............... 318/331, 443, 541, 491, 318/361

[56] References Cited

U.S. PATENT DOCUMENTS

| | | | |
|---|---|---|---|
| 2,474,830 | 7/1949 | Curry | 318/331 |
| 3,310,722 | 3/1967 | Diello | 318/331 |
| 3,512,068 | 5/1970 | Mori | 318/331 |
| 3,539,893 | 11/1970 | Tong | 318/331 |
| 3,602,290 | 8/1971 | Kearns | 318/361 |
| 3,681,620 | 8/1972 | Hoge | 318/341 |
| 3,876,919 | 4/1975 | Kearns | 318/331 |

*Primary Examiner*—B. Dobeck
*Attorney, Agent, or Firm*—Lane, Aitken & Kananen

[57] ABSTRACT

The condition of a surface is sensed by cyclically moving two members having engaged surfaces relative to each other, driving the surfaces for only a portion of each cycle to set up a threshold kinetic energy level in accordance with the friction between the engaged surfaces, sensing the kinetic energy developed in one of the members due to moving the members relative to each other, comparing the developed kinetic energy with the threshold kinetic energy and controlling the cyclic movement of the members in accordance with the relationship between the kinetic energy threshold and the developed kinetic energy. The cyclic movement of the members is then used to provide a visual indication of the condition of one of the surfaces.

12 Claims, 10 Drawing Figures

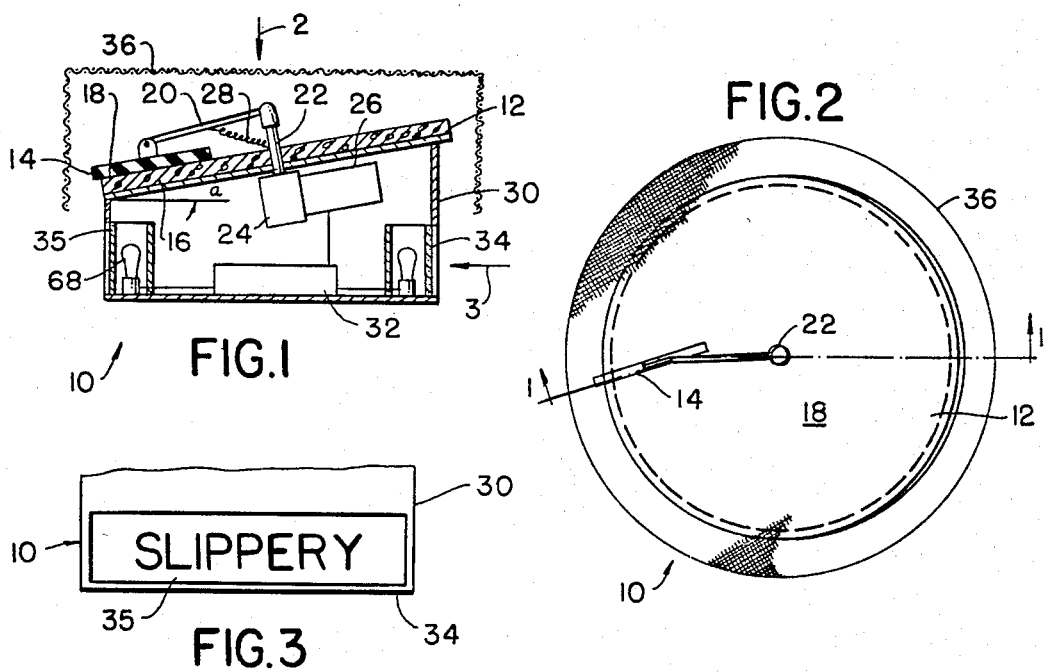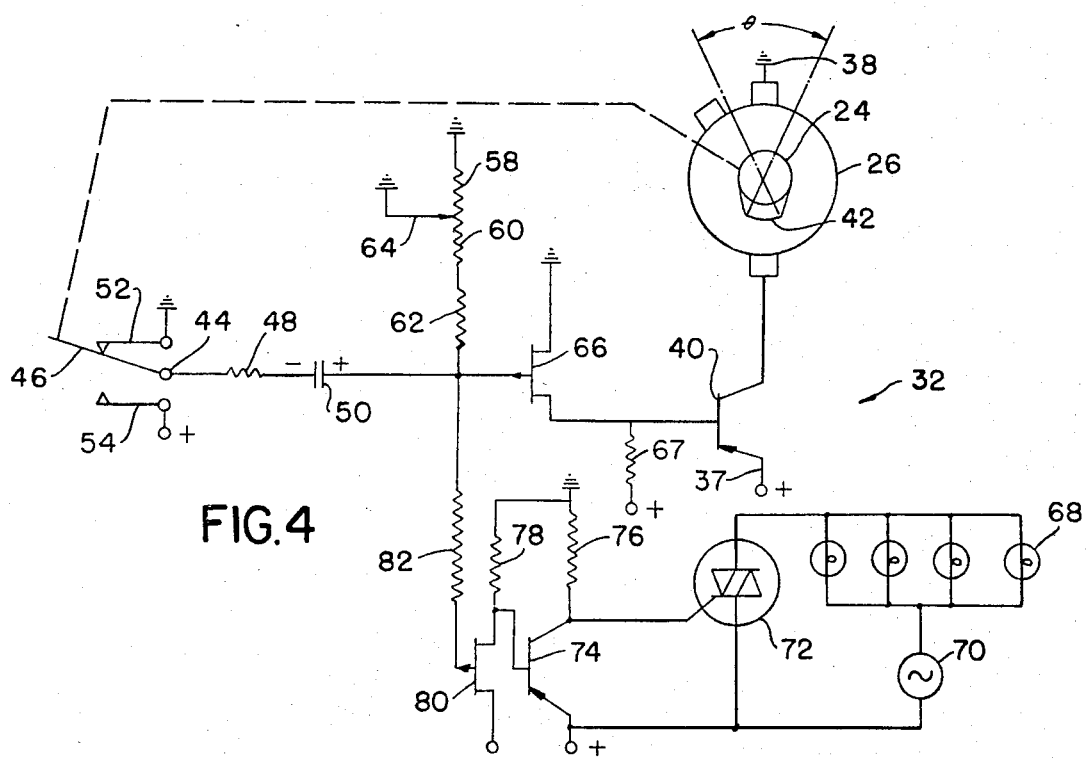

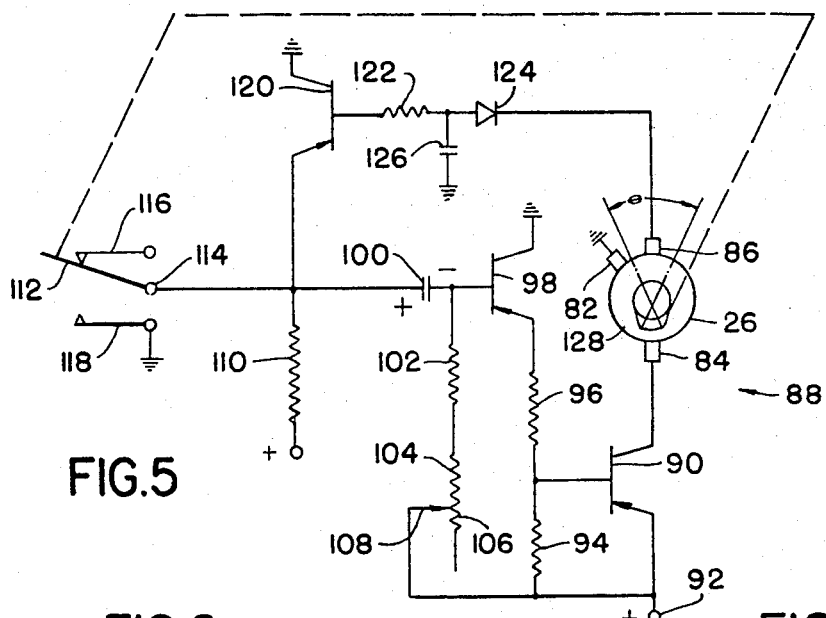
FIG.5
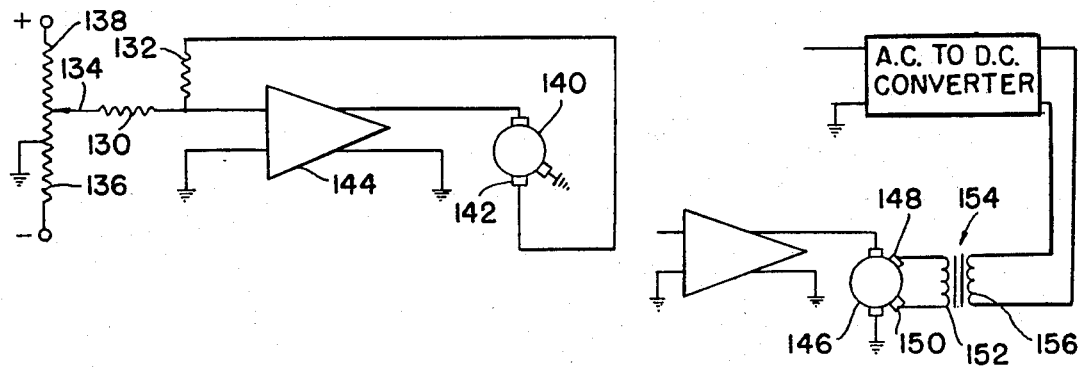
FIG.6 FIG.7
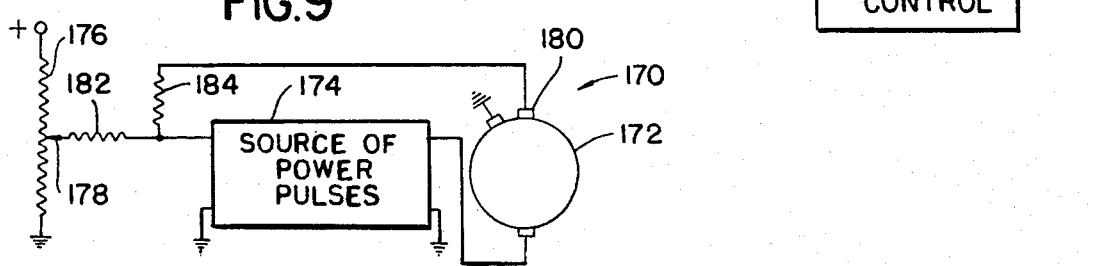
FIG.8
FIG.9

STRUCTURE FOR AND METHOD OF SURFACE CONDITIONING SENSING AND INDICATING AND MOTOR SPEED CONTROL

REFERENCE TO RELATED APPLICATIONS

This application is a continuation of application Ser. No. 957,775, filed Nov. 6, 1978, which is a continuation of application Ser. No. 814,000, filed July 8, 1977, which is a continuation of application Ser. No. 565,478, filed Apr. 7, 1975, which is a continuation of application Ser. No. 340,557, filed Mar. 12, 1973, now U.S. Pat. No. 3,876,919, which is a divisional of application Ser. No. 487,795, filed June 8, 1970, now U.S. Pat. No. 3,721,115, which is a continuation of application Ser. No. 666,703, filed Sept. 11, 1967, now abandoned.

BACKGROUND OF THE INVENTION

1. Field of the Invention

The invention relates to highway safety methods and structures and refers more specifically to determining the condition of a highway surface or the like and providing an indication thereof, particular structure for providing a signal proportional to the speed of an electric motor from the motor itself, and a method of and structure for motor speed control with the particular structure.

2. Prior Art

There is considerable emphasis today on highway safety. As a result, automobile manufacturers and highway engineers are attempting to improve the safety of both automobiles and highways. There are, however, many parameters of highway safety which are beyond the control of automotive and highway engineers. One of the significant parameters influencing highway safety is weather conditions. Weather conditions may produce particularly dangerous highways due to the degree of slipperiness of the road surface.

In the past, attempts have been made to determine the condition of a road surface and to warn approaching motorists when the road surface condition is dangerous. Such attempts have often taken the form of instruments for measuring the dew point and temperature to determine the existence of, for example, water or ice on a highway. However, such devices have not been the ultimate answer since highway surfaces may be slippery without water or ice thereon. For example, small granules of sand distributed on the surface of a highway will seriously reduce the coefficient of friction of the surface so that vehicle tires may slide on the road surface. Therefore, it is desirable to more exactly measure the coefficient of friction or slipperiness of a road surface rather than specific conditions thereof, such as the presence of water or ice thereon.

In addition, wherein motor speed control devices have been provided in the past, they have generally included separate equipment, such as tachometers to provide a feedback signal proportional to motor speed. Such additional equipment is expensive and not essential in motor speed control apparatus.

Also, prior speed controls for electric motors have not usually been fail safe. That is, they have not included structure for preventing operation of the motor if the motor speed control circuit malfunctions. A fail safe motor control circuit is particularly desirable in conjunction with electrically driven automobiles and the like.

SUMMARY OF THE INVENTION

The invention includes a structure for and method of sensing the condition of a surface, for example, a highway surface and providing a visual indication of the condition of the surface. A means for and a method of varying the visual indication of the conditiion of the surface in accordance with the surface condition is also provided.

The surface condition sensing structure includes an electric motor circuit in which an additional brush is engaged with the commutator which redistributes the current provided in the armature whereby a signal is available proportional to the speed of the motor which is part of the invention.

The motor speed signal developing circuit of the invention is particularly useful in providing an efficient, inexpensive method of and circuit for motor speed control in accordance with the invention. The motor speed control circuit of the invention includes fail safe structure to prevent operation of a motor controlled by the motor speed control circuit on failure of the motor speed control circuit.

DESCRIPTION OF THE DRAWINGS

FIG. 1 is a section view of structure for surface condition sensing and indicating in accordance with the method of the invention constructed in accordance with the invention.

FIG. 2 is a top view of the surface condition sensing structure illustrated in FIG. 1 taken in the direction of arrow 2 in FIG. 1.

FIG. 3 is a partial elevation view of the surface condition sensing structure illustrated in FIG. 1 taken in the direction of arrow 3 in FIG. 1.

FIG. 4 is a schematic diagram of the electrical portion of the structure for sensing surface conditions illustrated in FIGS. 1 through 3.

FIG. 5 is a schematic diagram of another embodiment of the electrical portion of the structure for sensing surface conditions illustrated in FIGS. 1 through 3.

FIG. 6 is a schematic diagram of structure for providing an electrical signal proportional to motor speed constructed in accordance with the invention in a motor speed control circuit for practicing the motor speed control method of the invention.

FIGS. 7 and 8 are partly schematic, partly block diagrams of modifications of the motor speed control circuit illustrated in FIG. 6.

FIG. 9 is a partially schematic, partially block diagram of yet another modification of the motor speed control circuit illustrated in FIG. 6, wherein the motor is energized by pulses of electrical energy.

DESCRIPTION OF THE PREFERRED EMBODIMENTS

Figure 10:
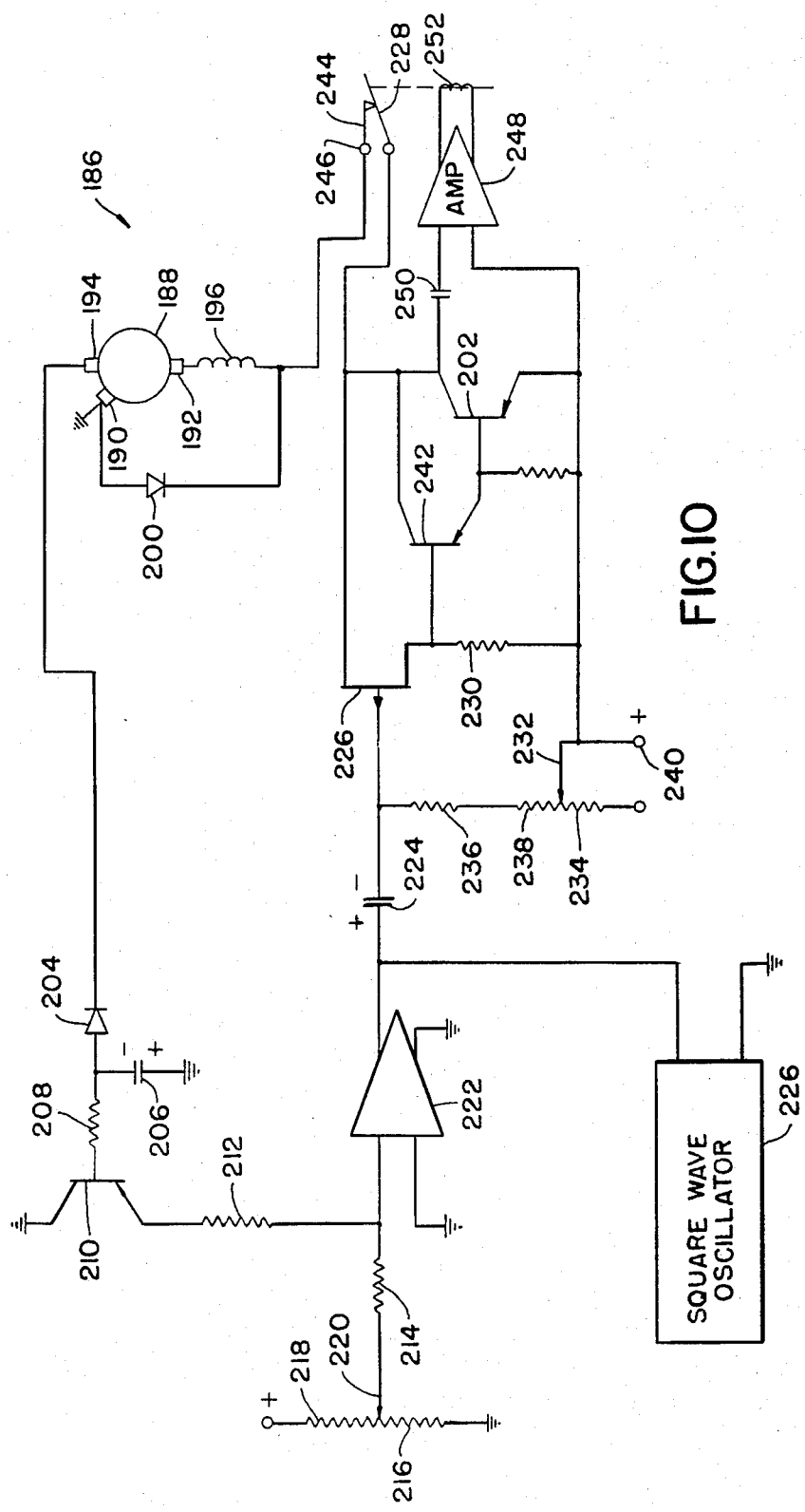
FIG. 10 is a detailed schematic diagram of one embodiment of the motor speed control circuit illustrated in FIG. 9.

The structure 10 for sensing and indicating a surface condition illustrated in FIG. 1 includes a disc member 12 of a first material which is the material the surface condition of which it is desired to sense and indicate. For example, the material 12 may be material the same as a highway surface adjacent which the structure 10 is positioned. The surface of the material 12 and the surface of the highway will then have the same coefficient of friction or the same slipperiness under the same conditions.

The structure 10 further includes the movable member 14 having a surface 16 in surface-to-surface engagement with the surface 18 of the disc 12 connected to the arm 20 for rotation about the drive shaft 22 extending from transmission 24 which is driven by the motor 26. The resilient means 28 is provided between the shaft 22 and the arm 20 for regulating the normal force with which the surface 16 engages the surface 18.

As shown best in FIG. 1, the material 12 is mounted at an angle α with respect to the horizontal and is supported on the frame 30 which encases the transmission 24, motor 26 and the electrical portion 32 of the structure 10. The indicating portion 34 of the structure 10 which, as shown, includes a sign 35 in front of lights 68 may also be enclosed by the frame 30, as will be understood by those in the art.

A guard 36 of expanded metal is provided, as shown in FIG. 1, to prevent placement of undesirable objects on the disc 12 which would give a false indication of a surface condition of, for example, a highway adjacent the structure 10. The diameter of the guard 36 in conjunction with the angle at which disc 12 is positioned with respect to the horizontal and the angle at which the member 14 is positioned with respect to the radius of the disc 12, together with the extension of the member 14 radially beyond the edge of disc 12, will maintain the surface of the disc 12 substantially clean. Thus, on each revolution of the member 14 on the disc 12, the disc 12 will be swept clean. Snow and other solids tending to accumulate thereon will pass between the outer periphery of the disc 12 and the guard 36. It is intended that the structure 10 be placed at a substantial height above the ground adjacent a highway to minimize the chance of tampering therewith and articles being placed thereon and to provide maximum visibility thereof.

The electrical portion 32 of the strcuture 10, shown best in FIG. 4, includes the motor 26 connected between a source of positive electric energy 36 and ground 38 in series with the emitter collector circuit of the transistor 40. A cam 42 is secured to the transmission 24 for rotation at the speed of the motor 26. The cam 42 is mechanically connected to the double throw switch 44. The movable contact 46 of the switch 44 is connected through a resistor 48 to one side of the capacitor 50. One fixed contact 52 of the switch 44 is connected to ground, while the other fixed contact 54 of the switch 44 is connected to the source of positive electric energy.

The circuit 32 further includes the potentiometer 58 having a resistor 60 in series with a second resistor 62 connected between ground and the other side of the capacitor 50. The wiper arm 64 of potentiometer 53 is connected directly to ground. A field effect transistor 66 having a source connected through resistor 64 to the source of positive electric energy and to the base of the transistor 40, a drain connected directly to ground and a gate connected directly to the junction between the resistor 62 and the other side of the capacitor 50 completes a control loop in the circuit of the motor 26.

The circuit 32 further includes a plurality of lamps 68 connected in parallel with each other and in series with a source of alternating electric energy 70 and a Triac 72. As shown, the control electrode of the Triac is connected to the emitter-collector circuit of a transistor 74. The emitter-collector circuit of the transistor 74 is connected in series between the source of positive electric energy and resistor 76. The resistor 76 is also connected to ground. The base of the transistor 74 is connected through the resistor 78 to ground and to the drain of a second field effect transistor 80. The second field effect transistor 80 includes a source connected to the source of positive electric energy and a gate connected through a resistor 82 to the gate of the field effect transistor 66 and the junction between the resistor 62 and the other side of the capacitor 50, as shown best in FIG. 4.

In overall operation of the structure 10, it is assumed that the cam 42 is out of the θ angle region so that the switch 44 is in the position illustrated in FIG. 4. Any time that the cam 42 passes through the θ angle in its rotation with the motor 26, the movable contact 46 of switch 44 will be connected to the positive source of electric energy through the contact 54. With the switch 44 in the position illustrated in FIG. 4, current will flow from the base of transistor 40 through field effect transistor 66 and the resistors 60 and 62 in series to ground. The transistor 40 will therefore be on so that the motor 26 will be driven and the capacitor 50 will be charging to a positive potential on the right side thereof.

Also, at this time the field effect transistor 80 will be turned on to provide a voltage on the base of the transistor 74, maintaining the transistor 74 in an off condition. With transistor 74 off, the Triac 72 is actuated by current through resistor 76, whereby the lights 68 are energized through the power supply 70 by Triac 72.

When the motor 26 rotates into the θ angle, the contact 46 of switch 44 engages the contact 54, whereby the positive voltage source is connected to the left side of the capacitor 50. Then, because the capacitor 50 cannot change its charge instantaneously a positive charge on the right hand side of the capacitor 50 equal to twice the positive voltage source will be present. Such charge on the right side of the capacitor 50 will cause the field effect transistors 66 and 80 to turn off.

The turning off of the field effect transistor 66 will turn off the transistor 40 to stop driving of the motor 26. The turning off of the field effect transistor 80 will cause conduction of the transistor 74 to place the gate electrode of the Triac 72 at the positive voltage source level to turn off the Triac 72 and disconnect the lights 68 from the power supply 70.

The field effect transistors 66 and 80 remain in the off condition until the capacitor 50 can discharge through a time constant, including the capacitor 50 and the resistances 60, 62 and 48 in series. If prior to timing out of the time constant the motor 26 turns sufficiently to move the cam 42 through the θ angle, the switch 44 will return to the position illustrated in FIG. 4 and the capacitor 50 will again start to charge, the field effect transistors 66 and 80 will turn on and a new cycle of operation of the structure 10 will begin.

In terms of the members 12 and 14, it will be understood that rotation of the motor 26 will rotate the member 14 in surface-to-surface engagement with the disc 12 to develop kinetic energy in the member 14. If during rotation of the motor 26, as the cam 24 moves into the θ angle, the kinetic energy in the member 14 is sufficient to move the member 14 through the θ angle against the retarding action of the frictional forces between the surfaces 16 and 18 to start a subsequent driving cycle of the motor 26 and member 14, the lights 68 will stay on substantially constantly. If however, the condition of the surface 16 of the disc 12 is such as to provide a high coefficient of friction so that little kinetic energy is developed in the member 14 during rotation thereof and high drag is present on the member 14 in the θ angle, the member 14 will stop in the θ angle some place and a subsequent cycle of operation of the structure 10 must await the discharging of the capacitor 50 through the resistance 62, 60 and 48.

The time constant of the capacitor 50 and of resistances 60, 62 and 48 may be considerable, that is, for example, ten minutes. It will, therefore, be understood that the lights 68 of the indicator 34 will illuminate the sign 35 substantially constantly when the surface 18 is of a condition such that the coefficient of friction thereof is so low that the member 14 will slide through the θ angle. When the kinetic energy of the member 14 is not equal to the threshold level of kinetic energy determined by the θ angle and the particular materials and structure 10 so that the member 14 stops within the θ angle during a cycle of operation of the structure 10, the lights 68 will be out substantially all of the time. That is, for example, with the member 14 making one revolution per second and with a time delay or dwell time of ten minutes, when the member stops in the θ angle, the lights 68 would be on only one six-hundredth of the time. Drivers observing the structure 10 and particularly the indicator 34 thereof would thus be warned of a surface condition on the highway matched by the surface condition of the disc 12 which provides a dangerously low coefficient of friction between the highway and automobile tires having substantially the same material composition as the member 14.

The circuit of FIG. 4 thus provides a slippery or non-slippery indication to a driver as a warning. It would, however, be desirable if the indication were more qualitative. That is to say, it would be of more information to a motorist if the length of time the indicator 34 were illuminated were related to the degree of slipperiness of the road surface. Thus, if the road is slippery enough and the surface 18 is in such a condition that the member 14 almost slips through the θ angle, it would be desirable to illuminate the indicator 34 for a longer period of time than when the surface 18 is not slippery, has a high coefficient of friction and the kinetic energy developed in the member 14 is considerably below the threshold value which would allow the member 14 to slip through the θ angle. The circuit of FIG. 5 will provide such operation of the apparatus 10.

In the circuit of FIG. 5, the motor 26 is a direct current motor, including an armature connected to a commutator and including at least two brushes 82 and 84 engaged with the commutator for passing a direct current motor driving signal through the armature of the motor 26. With such a motor 26, a third brush 86 positioned on the commutator will provide a signal proportional to the speed of the motor 26. In such structure, the motor 26 acts in the nature of a tachometer, wherein the section of the armature between brushes 82 and 86 is rotated in a fixed magnetic field to provide a signal proportional to the speed of rotation of the armature.

In using a tachometer to develop a signal proportional to motor speed the voltage developed is purely due to the rotation of the armature. However, when the motor 26 is used to provide a feedback signal representative of the speed of the motor through an additional commutator brush 86, the signal at the brush is a function of both current through the motor and the motor speed. That is to say, that the voltage across the motor armature is equal to the current through the armature times the resistance of the armature plus the back electromotive force in volts per radiance per second times the armature angular velocity in radiance per second. Thus, when the speed of the motor 26 is low and the current times resistance component is large a speed control signal based on the voltage across a portion of the armature is in error. However, with the brush 86 placed close to the ground brush 82, the current flowing therebetween is small so that the signal output from the brush 36 is close to a true function of motor speed.

The modified circuit 89, illustrated in FIG. 5, includes an additional brush on the commutator of motor 26 and the transistor 90 and having an emitter-collector circuit connected between the brush 84 of the motor 26 and a positive source of electric energy 92. The base of transistor 90 is connected between the resistors 94 and 96 as illustrated. A second transistor 98 has its emitter collector circuit connected between the resistor 96 and ground and includes a base connected to one side of a capacitor 100. The base of the transistor 98 is also connected through the resistor 102, the resistance 104 and wiper arm 103 to the source of positive electrical energy 92 and the other arm of resistor 94 as shown.

The left side of capacitor 100 is connected through a resistance 110 to the source of positive electric energy and to the movable center contact 112 of switch 114. Thus, when the cam 128 driven by motor 26 is outside of the θ angle, the contact 112 of switch 114 is in engagement with the dead contact 116 of the switch 114 and when the cam 126 is in the o angle, the contact 112 of the switch 114 is in engagement with the grounded contact 110 of the switch 114.

The circuit of FIG. 5 is completed by the transistor 120 having a grounded collector 120 and an emitter connected directly to the left side of the capacitor 100. The base of transistor 120 is connected through a resistor 122 and a filter network including a diode 124 and a capacitor 126 to the added brush 86 on the commutator of the motor 26.

In operation of the circuit of FIG. 5, when the motor 26 is rotating slowly, that is due to a high torque load thereon because of high friction between the surfaces 18 and 16 of members 12 and 14, a small feedback voltage will be fed from the third brush 86 on the commutator of motor 26 through the diode 124 and resistor 122 across capacitor 126 to the base of the transistor 120. The small voltage will not be sufficient to turn the transistor 120 on. Therefore, the junction between the resistor 110 and capacitor 100 will rise to the positive potential of the source of positive electric energy to charge the capacitor 100 positive on the left side and negative on the right side. The transistor 98 will thus be biased on and the transistor 90 will therefore also be on to provide driving current through the motor 26.

When the cam 128 is rotated into the θ angle, the contact 112 of the switch 114 is moved from the dead contact 116 to the grounded contact 118. The left side of the capacitor 100 is thus grounded so that a difference in potential of the value of the positive source of electric energy will appear across the capacitor 100. The transistor 98 is thus caused to turn off and will turn off the transistor 90 to prevent driving of the motor 26. The time delay will be shorter since the capacitor is not fully charged.

The transistor 93 will remain in the turned off condition until the charge on the capacitor 100 has been drained off through the resistance capacitance time constant provided by the resistors 102, 104 and 110 and the capacitor 100. This time constant can be changed by the position of the potentiometer wiper arm 103. When the transistor 93 is turned on, the lights 68 which may be connected as before to the right hand side of the capacitor 100 may be energized through a circuit, such as the bottom circuit of FIG. 4, to indicate a non-slippery surface by blinking only at large intervals.

Assume then that the surface 13 of member 12 is slippery, as when ice or water have collected thereon to substantially reduce the coefficient friction between the surfaces 16 and 18 and to increase the kenetic energy in the movable member 14 and the speed of the motor 26, the feedback voltage from the third brush 36 on the commutator of the motor 26 will be sufficient to turn on the transistor 120 so that the resistance offered by the transistor 120 and the resistor 110 will form a voltage divider to divide the voltage of the source of positive electric energy. The voltage at the junction between the resistor 110 and the left hand side of the capacitor 100 will then be determined by the feedback voltage from the motor 26 due to the degree of conduction of the transistor 120. That is to say, for example, if the motor 26 is running very fast, the transistor 120 will be turned full on and the left hand side of the capacitor 100 will be substantially at ground.

When the cam 128 passes through the θ angle, the switch 114 again places the left hand side of the capacitor 100 at ground through the contact 118. The charge on the capacitor 100 will then go from some positive potential to which it has been allowed to charge with transistor 120 on to ground on the left side during a time constant, again determined by the resistors 102, 104 and 110 and the capacitor 100. The transistors 98 and 90 will again be turned off during this period and the motor 26 will not be driven and the lights will not be energized.

Now, as the speed of the motor 26 is increased, that is as the surface 18 becomes more slippery, the initial charge on the capacitor 100 as the cam goes into the o angle will become smaller and the time that the transistors 98 and 90 are turned off will become progressively less until the lights 68 are energized substantially all of the time. Thus, the circuit of FIG. 5 will cause the lights 68 to be energized exactly in accordance with the speed of the motor 26 and the condition of the surface 18.

As indicated above, the including of an additional brush on the commutator of motor 23 will provide a signal which is proportional to motor speed. In FIG. 6 the feedback voltage provided from a third brush 142 on an electric motor is used to provide motor speed control.

In the circuit of FIG. 6, the resistors 130 and 132 provide a comparison between the desired speed represented by the position of the wiper arm 134 on the resistor 136 of potentiometer 138 with the feedback voltage from the motor 140 through the additional brush 142 on the motor commutator. The feedback signal through the resistor 132 is of a sign opposite of the signal through the resistor 130. The difference between these two signals to provide a control signal may be very small if the amplifier 144 has a high gain or in other words is a very large transfer function. The current through resistors 130 and 132 would in such structure be substantially equal when the motor 140 is running at the regulated speed therefor.

When the speed of rotation of the motor 140 is reduced, as for example by a heavy load, the feedback signal would be reduced to provide an increased signal through the amplifier 144 to drive the motor 140 harder and thus increase the speed thereof to bring it back to the regulated speed. Similarly, when the motor speed is too high, the error signal provided the amplifier 144 will be such as to slow the motor down to bring it back to the regulated speed.

The feedback signal from the motor 140 will be a complex signal having both an alternating and direct component due to the usual commutator structure. If it is desired to operate with only the alternating feedback signal, a circuit, such as illustrated in FIG. 7 may be used, wherein a pair of additional brushes 148 and 150 are provided on the commutator of the motor 146 which brushes are connected to the primary winding 152 of transformer 154 having the secondary winding 156. The purely alternating feedback signal component is then passed through the alternating to direct signal converter to provide operation of the speed control, as in FIG. 6.

Also, as indicated in FIG. 8, by varying the location of a plurality of auxiliary brushes 158, 160, 162 and 164 on motor 166 different magnitude feedback signals, each proportional to motor speed, may be tapped from the motor 166. These feedback voltages may as indicated be used to energize auxiliary control units which would then respond to the speed of rotation of the motor 166.

Considering motor speed control through the use of auxiliary brushes on the commutator of electrical motors further, it will be understood that the most efficient way of controlling a direct current motor is with pulses of electrical energy. With such speed controls, transistors are normally used as switching devices. One such motor speed control 170 is illustrated generally in FIG. 9, wherein the motor 172 is controlled by pulses from the source of power pulses 174 in accordance with the voltage comparison between the voltage tapped from potentiometer 176 by wiper arm 178 and the electric signal tapped from the motor 172 through the brush 180 across the resistors 182 and 183. These pulsed, transistor controlled systems are particularly efficient since when the current through the motor is high, the voltage drop across the transistors supplying the current is small and when the current through the motor is small, the voltage drop across the controlling transistors is high and the voltage drop across the motor is small. Consequently the power loss in such systems is limited to a very short time in which the transistor is switching.

In addition, it will be remembered that the motor is basically an integrator in conjunction with such systems. Consequently the power pulses for driving the motor 172 are smoothed by the motor. If the frequency is high enough, it is then difficult to detect that the motor is not drawing power and rotating continuously. Due to this smoothing action of the motor, the signal generated at the third brush 180 is going to be smooth. Consequently, by using pulse width modulation to vary the power to the motor efficiently and by using a third brush to obtain effective tachometer feedback, an efficient well regulated speed control 170 is achieved.

By operating the source of power pulses at as low a frequency as reasonable to obtain smooth operation, power loss in the system is minimized. By operating the source of power pulses or oscillator at near a constant frequency, smooth operation of the speed control is achieved over its operating range. Thus, at start-up, the motor initially turns slowly and is receiving power pulses at a high pulse per revolution rate. At high speed, the motor receives power pulses at a low pulse per revolution rate which enhances the efficiency of the speed control as described above. At high speed, the high momentum of the system allows smooth operation with power pulses at a low effective pulse rate.

A pulse controlled motor speed control 186 having fail safe features is illustrated in more detail in FIG. 10. In the motor speed control structure of FIG. 10, the motor 188 is provided with the usual commutator brushes 190 and 192 and with the third commutator brush 194 for again providing a signal proportional to motor speed. The motor 188 is illustrated as having a series field 196 although the indicated speed control could be used equally well with a motor having a permanent magnet field. The diode 200 is a smoothing diode which provides a current with the transistor 202 turned off.

The feedback signal from the motor 188 is again passed through the filter and current limiting circuit, including the diode 204 and capacitor 206 and the resistance 208. Again, when the motor 188 is rotated at a sufficient speed, the transistor 210 will be turned on to provide a current flow through resistor 212 proportional to the feed-back signal from the motor 188 for comparison with the electric signal 214 tapped from the resistor 216 of the potentiometer 218 having a wiper arm 220. The difference in the electrical signals through the resistors 212 and 214 is passed through the high gain transfer circuit 222 to again charge the left side of capacitor 224 positive an amount depending on the speed of the motor 188. It will be noted that the capacitor is charged while the motor is coasting so that the charge on the capacitor is more indicative of purely motor speed. That is to say, it is not affected by a power current burst.

The square wave oscilator 226 is provided to return the capacitor 224 to ground periodically, causing a voltage change on the right hand side of the capacitor 224 sufficient to cause conduction of the field effect transistor 226 having a gate electrode connected to the right side of capacitor 224 and having source and drain electrodes connected to the movable contact of switch 228 and through resistor 230 to the wiper arm 232 of potentiometer 234. The field affect transistor 226 will remain turned on for a time determined by the time constant of the capacitor 224 and the resistance 236 and the resistor 238 of the potentiometer 234. As shown, the wiper arm 232 of the potentiometer 234 is connected back to the source of positive electric energy 240.

When the field effect transistor 226 is turned on, the transistor 242 and transistor 202 connected as shown are turned on to provide current through the transistor 202 and the contacts 228 and 244 of the switch 246 to energize the motor 188. The pulse width of the motor energizing pulse through the switch 246 may be regulated by the position of the potentiometer wiper arm 232 and motor speed control may be effected as before.

It will however be noted that in the motor speed control circuit of FIG. 10 that a pulse of motor energy is provided during the power pulse which accompanies a control pulse, wherein in the motor speed control circuit of FIG. 5 the control pulse kept the power to the motor off. The circuit of FIG. 10 thus has an advantage in the event that the control is used to drive a vehicle since a loss of control pulses would turn the vehicle's power off. That is the control circuit of FIG. 10 is fail safe. Should the control circuit of FIG. 10 fail by, for example, having the field effect transistor 226 or the transistors 242 or 202 short, the alternating current amplifier 248 would no longer receive pulses from the transistor 202 through the coupling capacitor 250 and would cause the relay 252 to open the switch 246.

While one embodiment of the present invention and modifications thereof have been disclosed in detail, it will be understood that other embodiments and modifications are contemplated by the inventor. It is therefore the intention to include all embodiments and modifications as are defined by the appended claims within the scope of the invention.

What I claim as my invention is:

1. A motor-signal generator system comprising a direct current motor including a commutator and having three brushes contacting the commutator, an energy source, a first electrically conductive circuit means connected to two of said three brushes for energizing said motor-signal generator and a second electrically conductive circuit means connected to the third and one other of said three brushes for deriving a signal generated within the motor-signal generator when the motor is rotationally displaced, said signal having an alternating current component, said second electrically conductive circuit means including means for obtaining the alternating current component of said signal.

2. In a motor system for driving an output intermittently in complete steps, comprising a direct current motor including a commutator and having three brushes contacting the commutator, a source of energy, a first electrically conductive circuit means connected to two of three brushes for de-energizing said motor automatically near the end of each step for a dwell period and automatically energizing said motor after said dwell period to start the next step, capacitive timing means to determine said dwell period, motor driven switch means operably associated with said first electrically conductive circuit means so energy is provided to said motor whenever said output is within a step and energy is not provided to the motor during a dwell period, a second electrically conductive circuit means connected to the third and one other of the said three brushes for deriving a signal generated within the motor operably associated to condition the capacitor such that when the signal is larger, the dwell time is shorter.

3. A motor system for driving an output intermittently in complete steps, comprising a direct current motor including a commutator and having three brushes contacting the commutator, a current source, a first electrically conductive circuit means connected to two of three brushes for de-energizing said motor sutomatically near the end of each step for a dwell period, capacitive timing means to determine said dwell period, motor driven switch means operably associated with said current source so the current flow is synchronized with the position of said output, supplying current to the motor when the output is within a step and stopping the flow of current to the motor for said dwell period, a second electrically conductive circuit means connected to the third and one other of said three brushes for deriving a signal generated within the motor and used to condition said capacitor such that when a step is traversed in less time, the dwell time is less.

4. In a motor system as described in claim 2, wherein the motor driven switch means is at ground potential during a dwell period.

5. In a motor system as described in claim 2, wherein the dwell time is reduced to zero when the signal generated exceeds a predetermined value.

6. A motor-signal generator system comprising a direct current motor including a commutator and having three brushes contacting the commutator, an energy source, a first electrically conductive circuit means connected to two of said three brushes for energizing said motor-signal generator, a second electrically conductive circuit means connected to the third and one other of said three brushes for deriving a signal generated within the motor-signal generator when the motor is rotationally displaced, said system including pulse width modulation means whereby said signal generated within the direct current motor modulates the time interval of the energizing of the motor.

7. The system of claim 6, wherein as the signal generated in the direct current motor becomes larger in magnitude as the time interval during which the motor is de-energized becomes larger.

8. A motor-signal generator system comprising a direct current motor including a commutator and having four brushes contacting the commutator, an energy source, a first electrically conductive circuit means connected to two of said four brushes for energizing said motor-signal generator, and a transformer primary forming a second electrically conductive circuit with the other two brushes for deriving in the secondary of said transformer an alternating component of a signal generated within the motor-signal generator when said motor-signal generator is rotationally displaced.

9. The system of claim 8 and further including an alternating current to direct current converter in circuit with the secondard of said transformer to provide a direct current signal proportional to the alternating current component of the signal generated within the motor-signal generator.

10. A motor-signal generator system comprising a direct current motor including a commutator and having three brushes contacting the commutator, an energy source, a first electrically conductive circuit means connected to two of said three brushes for energizing said motor-signal generator, a second electrically conductive circuit means connected to the third and one other of said three brushes for deriving a signal generated within the motor-signal generator when the motor is rotationally displaced, and capacitor means for conditioning the derived signal to control an operation in response to the rate of rotation of the motor.

11. The system of claim 10, wherein the operation controlled is the rate of rotation of the motor.

12. A motor-signal generator system comprising a direct current motor including a commutator and having three brushes contacting the commutator, an energy source, a first electrically conductive circuit means connected to two of said three brushes for energizing said motor-signal generator, a second electrically conductive circuit means connected to the third and one other of said three brushes for deriving a signal generated within the motor-signal generator when the motor is rotationally displaced, reference signal means, comparator means comparing the signal generated within the direct current motor with the output of said reference signal means to form a comparator output, and amplifying means amplifying the comparator output and modulating the energization of the motor with the amplified comparator output.

* * * * *